United States Patent [19]
Kehr et al.

[11] Patent Number: 6,085,752
[45] Date of Patent: Jul. 11, 2000

[54] METHOD, APPARATUS AND OPERATING SYSTEM FOR MANAGING THE ADMINISTRATION OF MEDICATION AND MEDICAL TREATMENT REGIMENS

[75] Inventors: Bruce A. Kehr, Potomac, Md.; Evan Sohn, New York, N.Y.; James E. Starnes, Crownsville, Md.; David Maurer, Randolph, N.J.; Irwin D. Baumel, Delray Beach, Fla.; David S. Stempler, Potomac, Md.

[73] Assignee: Informedix, Inc., Rockville, Md.

[21] Appl. No.: 09/398,816

[22] Filed: Sep. 20, 1999

Related U.S. Application Data

[62] Division of application No. 08/924,917, Sep. 8, 1997, Pat. No. 5,954,641.
[60] Provisional application No. 60/025,700, Sep. 9, 1996.
[51] Int. Cl.[7] ................................................. A61B 19/00
[52] U.S. Cl. .......................................... 128/897; 128/920
[58] Field of Search ............................ 600/300; 128/897, 128/920

[56] References Cited

U.S. PATENT DOCUMENTS

| | | |
|---|---|---|
| 4,004,577 | 1/1977 | Sarnoff . |
| 4,768,176 | 8/1988 | Kehr et al. . |
| 4,768,177 | 8/1988 | Kehr et al. . |
| 5,019,974 | 5/1991 | Beckers . |
| 5,200,891 | 4/1993 | Kehr et al. . |
| 5,408,443 | 4/1995 | Weinberger . |
| 5,596,994 | 1/1997 | Bro . |
| 5,612,869 | 3/1997 | Letzt et al. . |
| 5,642,731 | 7/1997 | Kehr . |
| 5,710,178 | 1/1998 | Samid . |
| 5,710,551 | 1/1998 | Ridgeway . |
| 5,722,418 | 3/1998 | Bro . |
| 5,769,793 | 7/1998 | Pincus et al. . |

*Primary Examiner*—William E. Kamm
*Attorney, Agent, or Firm*—McDermott, Will & Emery

[57] ABSTRACT

A medical monitoring device, operating system, and method is provided for managing administration of medical treatment regimens for treating a patient's medical conditions. The device stores medication schedule data, treatment data, patient query data, and patient response data. The device includes a controller for controlling modes of operation of the device, controlling access of the memory, controlling display of the treatment data and the patient query data on a display, receiving and processing patient response data, tracking timing, and providing scheduled medication alarm signals. The device further includes dedicated keys interfaced with the controller. Each dedicated key is associated with one of the medical treatment regimens, and initiates the display of treatment messages relating to the associated medical treatment regimen. Successive actuation of each dedicated key initiates the display of further treatment messages relating to the associated medical treatment regimen. The device further includes soft function keys interfaced with the controller. The soft function keys signal the controller, commanding it to execute different modes of operation of the medical monitoring device. The device provides scheduled medication alarm signals that alert the user concerning prescribed medications due to be taken.

18 Claims, 17 Drawing Sheets

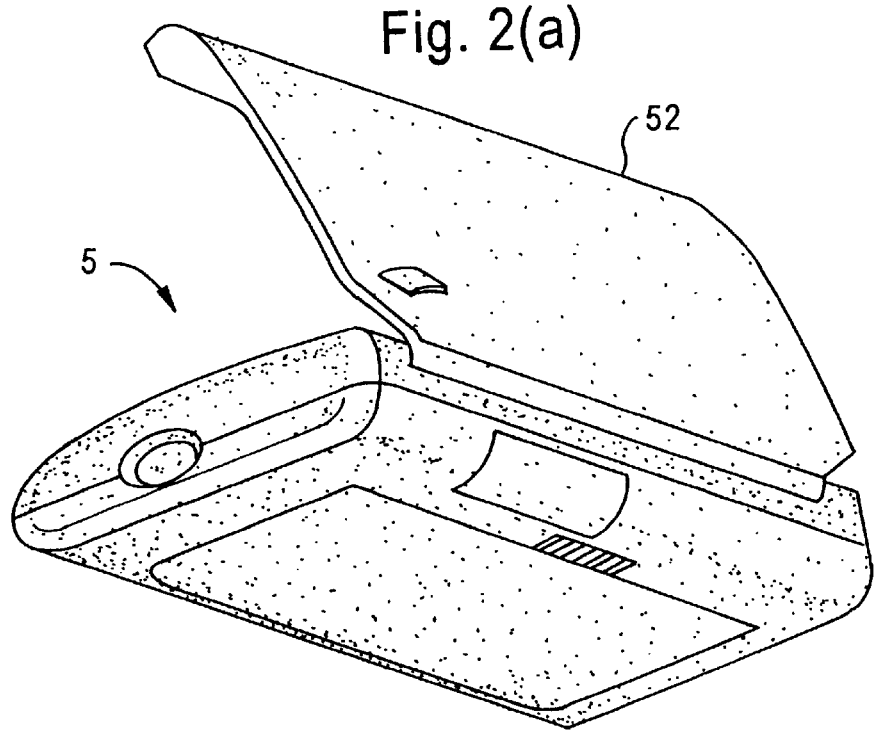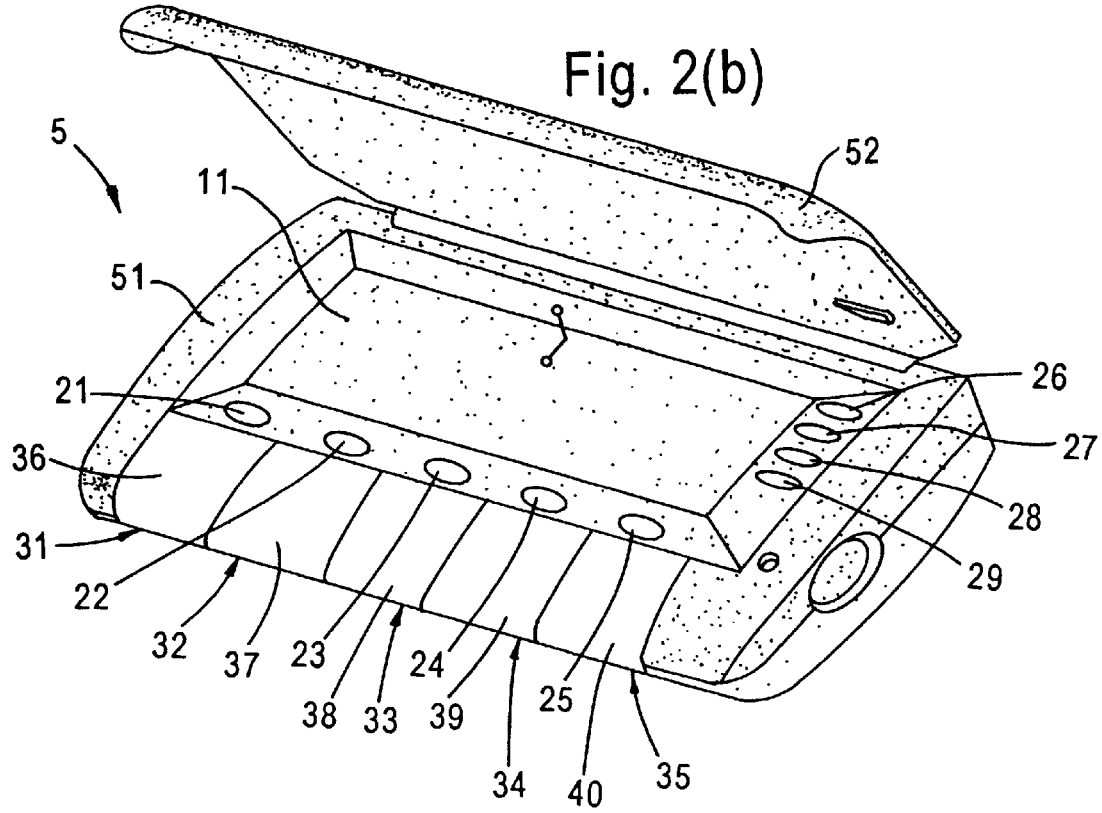

Questionnaire

Are you ready to answer some questions

Yes
No

Fig. 12(a)

Waking up with shortness of breath ?

Mild
Moderate
Severe
None

Fig. 12(b)

Questionnaire - General Health

Are you feeling...

Better
Worse
Same
Don't Know

Fig. 12(c)

Questionnaire - General Health

Weakness, fatigue...

None
Mild
Moderate
Severe

Fig. 12(d)

METHOD, APPARATUS AND OPERATING SYSTEM FOR MANAGING THE ADMINISTRATION OF MEDICATION AND MEDICAL TREATMENT REGIMENS

Priority is claimed under 35 USC 119(e) of Provisional Application No. 60/025,700, filed Sep. 9, 1996, division of Ser. No. 08/924,917, filed Sep. 8, 1997, and now U.S. Pat. No. 5,954,641.

FIELD OF THE INVENTION

The present invention relates to the field of medical devices for assisting with the administration of prescribed medication and medical treatment regimens, and monitoring medical treatment progress.

BACKGROUND OF THE INVENTION

The prior art discloses a number of electronic devices that assist with the administration of prescribed medication and monitor the medical treatment progress. Medication monitoring devices such as those disclosed in U.S. Pat. Nos. 5,200,891 and 5,642,731 provide a number of functions for facilitating patient adherence to prescribed therapies, and for facilitating cross-correlation of compliance data and clinical information about the patient.

Such devices have a plurality of medication compartments, a microprocessor with associated circuitry for providing timing signals, signals and display messages and for reading inputs from buttons that convey programming and operating information. They rely on programmed schedules for providing audible and/or visual alert signals at the scheduled times for taking certain medications and indicate the specific compartment from which the particular medication is to be taken, and quantity to be taken. The device of U.S. Pat. No. 5,642,731 is also capable of collecting contemporaneous data concerning the patient's adherence to the medication schedule, the progression of the medical condition(s) being treated, symptoms and side effects the patient is experiencing and other information pertinent to monitoring and treating the patient's medical condition(s).

However, the prior art suffers from a number of inherent disadvantages that have been solved by the present invention. The prior art devices contain complex operating systems rendering them difficult to understand how to operate and extract medical and educational information, and lack the functionality for easily presenting patient queries and obtaining patient responses, and easily communicating with remote devices. The operating systems of the prior art devices are also inadequate in their ability to provide for differentiation of operating sequences pertinent to specific medications and treatment progress, further complicating their operation and monitoring of treatment regimens.

Further, the prior art devices lack the ability to easily gather contemporaneous data reflecting treatment progress and actual patient behavior for adjusting subsequent treatment routines accordingly. The prior art devices also fail to provide the ability to easily deliver positive and negative feedback and warnings to the patient based upon actual patient behaviors related to their medication and their health. The prior art devices also fail to provide for automatic communication and transfer of data and information between the device and remote devices.

With regard to the identification of the medications stored in the device, the prior art lacks the ability to provide for easy identification of the medication contained in each compartment. Additionally, the prior art devices include fixed volume medication storage capacities that limit the device's flexibility and portability, and are unable to easily provide the patient with reminders as to when to reload specific medication(s), which medication compartments to reload, how many to reload, and what the medication looks like. Finally, the prior art devices suffer from a difficulty in giving repetitive reinforcing information on a per-medication basis, to encourage better compliance with the entire medical treatment regimen.

In view of the foregoing prior art disadvantages, it is an object of the present invention to provide a medical monitoring device, operating system and communication system that is simple to operate, and a method for managing the administration of prescribed medication(s) and treatment regimens for a patient's medical condition(s). Accordingly, the present invention provides advantages over the prior art devices by facilitating easy access to medication-specific, disease-specific and treatment-specific information, and by including functionality for easily presenting patient queries and obtaining patient responses. Further, the operating system of the present invention provides advantages over the prior art devices through clearly differentiating between operating sequences associated with each specific medication, further simplifying the device's operation and management of treatment regimens. Also, the present invention easily provides the patient with reminders as to when to reload specific medication(s), which medication compartments to reload, how much medication to reload, and what the medication looks like, even further simplifying the device's operation and management of treatment regimens.

It is a further object of the present invention to provide a medical monitoring device, operating system and method for managing the administration of prescribed medication(s) and treatment regimens capable of easily gathering, storing and communicating contemporaneous data reflecting treatment progress and actual patient behaviors. Accordingly, the present invention provides advantages over the prior art devices by enabling a health care professional to monitor treatment progress based on the communicated contemporaneous data via a cradle-based modem system or infrared communication system, to provide for the adjustment of subsequent treatment routines accordingly.

It is a further object of the present invention to provide a feature that, based upon patient behavioral data, presents the patient or caregiver positive and negative feedback concerning the patient's medication and medical condition(s). The present invention further includes features that provide repetitive reinforcing information on a per-medication basis. Accordingly, the present invention provides advantages over the prior art devices by encouraging better compliance with the entire medical treatment regimen managed by the device.

It is a further object of the present invention to provide a medical monitoring device, operating system and method for managing the administration of prescribed medications and treatment regimens that facilitates easy identification and identifying characteristics of the medication contained in each device compartment. The present invention also provides for variability in the volume capacities of the medication compartments which expands the device's flexibility and portability over the prior art.

The present invention provides advantages over the prior art devices by providing for simple operation and facilitating maximized efficiency and effectiveness in administering treatment regimens.

Additional objects and attendant advantages of the present invention will be set forth, in part, in the description that follows, or may be learned from practicing or using the present invention. The objects and advantages may be realized and attained by means of the instrumentalities and combinations particularly pointed out in the appended claims. It is to be understood that the following general and detailed descriptions are exemplary and explanatory only and are not to be viewed as being restrictive of the invention, as claimed.

SUMMARY OF THE INVENTION

The present invention relates to a portable electronic medical device that manages and monitors the administration of medical treatment regimens, and provides a patient user easy access to important information necessary for efficient and improved monitoring, treatment and management of the patient's medical condition(s) and health. The invention also collects information concerning the treatment of the patient's medical condition(s) to assist the health care professional in monitoring the progression of the patient's medical condition(s) and treatment results. The invention will collect contemporaneous information concerning the patient's adherence to the medication regimen, the progression of the patient's medical condition, the symptoms and side effects being experienced by the patient, other health status information, physiologic information (i.e. blood pressure or glucose levels) and the patient's general quality of life. This information will facilitate more immediate and accurate analysis of the patient's progress, which will result in more efficient management of the patient's medical condition, health and improved treatment results. The information is communicated to the health care provider through a communication base unit or cradle that interfaces with the device and transfers data to and from remote devices.

The device of the present invention provides a dedicated key, button, or touch point on a screen associated with each medication or disease. Each of the dedicated keys facilitates accessing information related to the associated medication or disease (i.e. electronic prescription labeling, pictures and color of the medication, description of the medication's function, conditions or diseases that the medication treats, side effects associated with the medication, drugs with which the medication interacts, etc.). An additional set of soft keys, buttons or touch points facilitates additional functionality (i.e. flexible applications, programming, switching between modes of operation, response to patient queries, accessing additional information regarding unscheduled and missed doses, communicating with remote devices, scrolling through additional messages, etc.).

The present invention further provides for a variable capacity compartment tray and storage system that affords complete flexibility in the quantities and volumes of solid, liquid or aerosolized doses contained within the unit. The variable capacity compartment tray also provides for pre-loading, and pre-labeling of medications. Accordingly, when the patient exhausts a supply of medication in one tray, a second pre-loaded and pre-labeled tray can quickly and easily replace the exhausted tray.

Additionally, the present invention provides a graphic display, allowing for the display of graphic images or text in any language, and allowing for a symbolic or pictorial set of instructions for illiterate patients. The graphics display can display graphic images that indicate the patient's progress. For example, if the patient is adhering to the treatment regimen, the graphic image may comprise a representation of the patient's body showing improved health and wellness, or a smiling face, or other symbols of improving health, wellness or achievement. Likewise, if the patient is not adhering to the treatment regimen, the graphic image may comprise a representation of declining health and wellness, or a frowning face, or other symbols of declining health, wellness or achievement. An algorithm in the device itself automatically and periodically updates or changes the graphic images, based upon the record of the patient's behavioral adherence to the treatment regimen collected and stored in the device.

In addition in the current rendition a software algorithm automatically adjusts future dosing regimens and instructions, based upon the patient taking previous doses too early, too late, or not at all; and additionally based upon the pharmacokinetic properties aspects of a particular drug contained within a particular compartment.

Finally, the present invention tracks the patient's consumption of each medication, and provides the patient "supply-to-load" reminders. The supply-to-load reminders tell the patient when to reload medication, which medication to reload, the quantity to re-load, when to call the health care provider or pharmacy for refills, etc. The device either automatically presents the supply-to-load messages, or presents the supply-to load messages when the patient presses a dedicated key for a particular medication.

BRIEF DESCRIPTION OF THE DRAWINGS

FIGS. 2(a) and 2(b) illustrate a top/side view and a bottom/rear/side view of the medical monitoring device of the present invention, including the dedicated and soft function keys, display, and infrared communications port.

FIGS. 12(a)–(d) illustrate the liquid crystal display, dedicated keys and soft function keys during a "Patient Query" mode operating sequence of the medical monitoring device, operating system and method of the present invention.

DETAILED DESCRIPTION OF EXEMPLARY EMBODIMENTS

All patents, patent applications and literatures cited in this description are incorporated herein by reference in their entirety. In the case of inconsistencies, the present disclosure, including definitions, will prevail.

The present invention provides an electronic device, operating system and method that assists a patient user with the administration of medical treatment regimens, and assists health care providers with providing the most efficient and effective treatment for medical conditions. Similar devices are disclosed in U.S. Pat. Nos. 5,200,891 and 5,642,731 incorporated herein by reference in their entireties.

Figure 1:
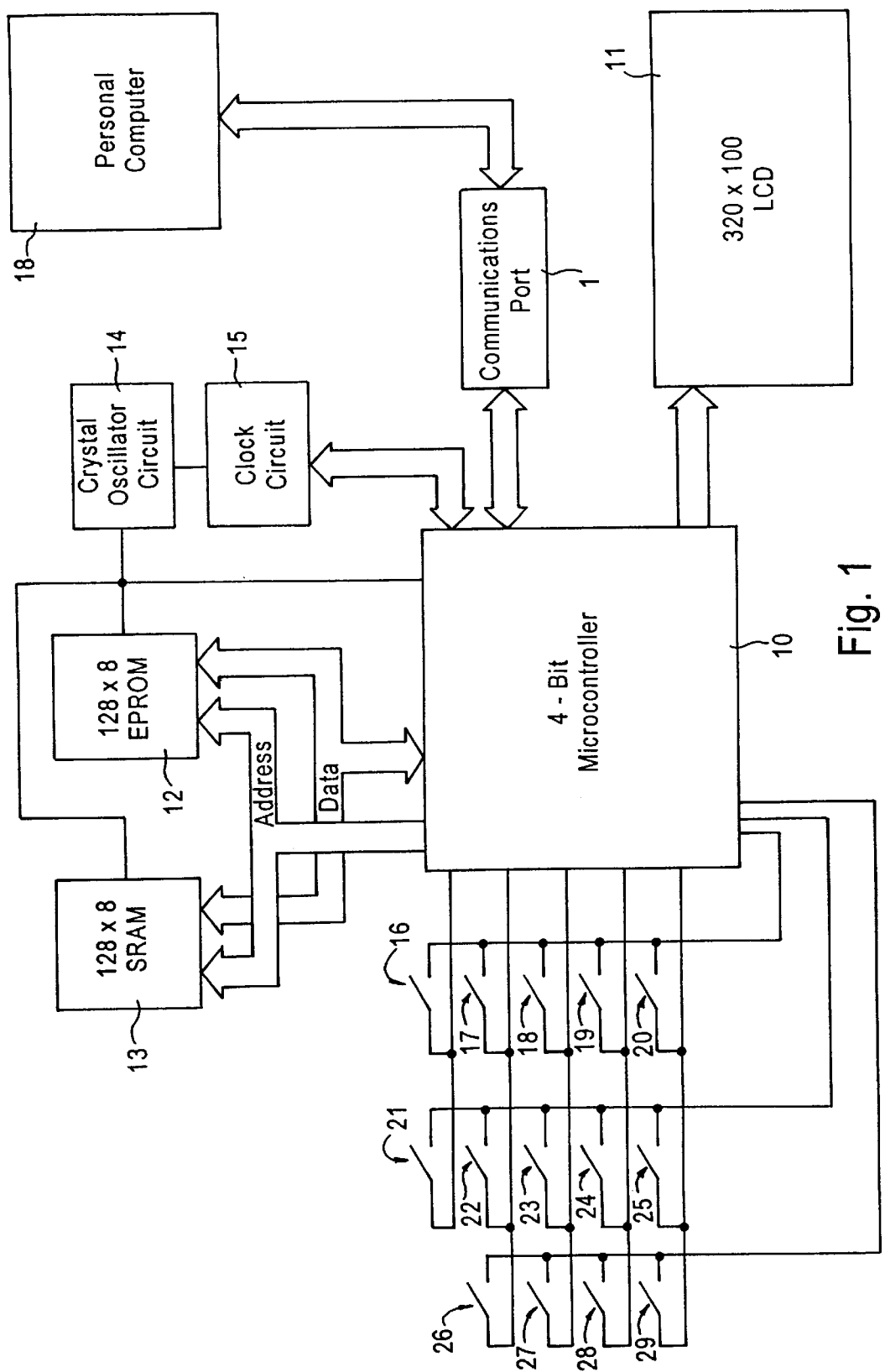
FIG. 1 illustrates a block diagram of the electronic circuitry of the medical monitoring device of the present invention.

In one exemplary embodiment, as illustrated in FIG. 1, the medical assistant device of the present invention utilizes a 4-bit microcontroller chip 10 interfaced with a 320×100 pixel liquid crystal display 11 ("LCD") with graphics capabilities. The device operating system is stored in a 128×8 bit external EPROM 12 and the variable data (i.e. medication scheduling data, treatment information, patient query data, and patient response data) is stored in an external 128×8 bit SRAM 13. The crystal oscillator circuit 14 provides a clock signal to the microcontroller 10, the clock circuit 15 tracks the date and time of day. Five compartment switches 16–20, five dedicated keys 21–25 and four soft function keys 26–29 are connected to inputs of the microcontroller 10 for supplying status signals, function commands and patient query responses to the microcontroller 10 for processing.

The device enables interaction with health care providers through a communication port 17. Communication port 17 comprises an infrared input/output port capable of communicating directly with a personal computer 18. In another embodiment, the communication port may comprise a serial port capable of communicating with a modem or directly with a PC.

The health care provider can download information to the device, such as programming data concerning the prescribed medication schedules, information concerning the prescribed medication and medical condition(s) being treated, and patient queries associated with the medical condition being treated. The health care provider can also upload information from the device, such as data concerning the patient's adherence to the prescribed medication schedules and information representing the patient's responses to patient queries.

The device itself, as illustrated in FIGS. 2(a) and 2(b), has a top face 51. The top face 51 includes openings for the LCD 11, dedicated keys 21–25, soft function keys 26–29 and medication compartments 31–35. The medication compartments 31–35 have respective compartment doors 36–40 covering them. The device also has a hinged top cover 52 for opening and closing the device. The medication compartments 31–35 are housed in a tray that inserts into the bottom of the device. The tray may be of various sizes, and may even be large enough to maintain a pill bottle, a medication inhaler, syringe, etc.

Compartment switches 16–20 signal the microcontroller 10, indicating when compartment doors are opened and closed. Each of the medication compartments 31–35 and its respective compartment door is associated with a compartment switch that senses the opening and closing of the compartment door. When a particular compartment door is opened, the associated compartment switch signals the microcontroller 10, and the microcontroller processes the signal according to the specific status of the device at that time. For example, as described in detail below, if a compartment door is opened during a scheduled medication alarm, the microcontroller 10 interprets this as an indication that the patient has complied with the prescribed schedule for the particular medication contained in that compartment. The compartment switches thereby facilitate the device's tracking of the patient's adherence to prescribed medication schedules.

The device provides a means for interacting with the patient through a series of operations controlled by the dedicated keys 21–25 and soft function keys 26–29. The dedicated keys 21–25 enable the patient to retrieve information concerning specific medications contained in the device's medication compartments or concerning specific diseases. The soft function keys 26–29 enable the patient to respond to patient queries concerning medication side effects, adherence to medication schedules, treatment progress, health status assessment and patient's quality of life. The soft function keys 26–29 further facilitate other operations, such as a programming mode for modifying device settings and adjusting medication schedules and treatment data, and other types of information capture. An alternative embodiment of the present invention employs points on a touch screen that function in the same manner as the dedicated keys 21–25 and soft function keys 26–29.

Each of the dedicated keys is associated with the particular medication compartment located adjacent to it. Specifically, dedicated key 21 is associated with medication compartment 31, dedicated key 22 is associated with medication compartment 32, dedicated key 23 is associated with medication compartment 33, dedicated key 24 is associated with medication compartment 34, and dedicated key 25 is associated with medication compartment 35. Each dedicated key controls the display or entry of information related to the specific medication stored in its associated medication compartment or related to the medical condition for which that medication is prescribed.

Figure 4:
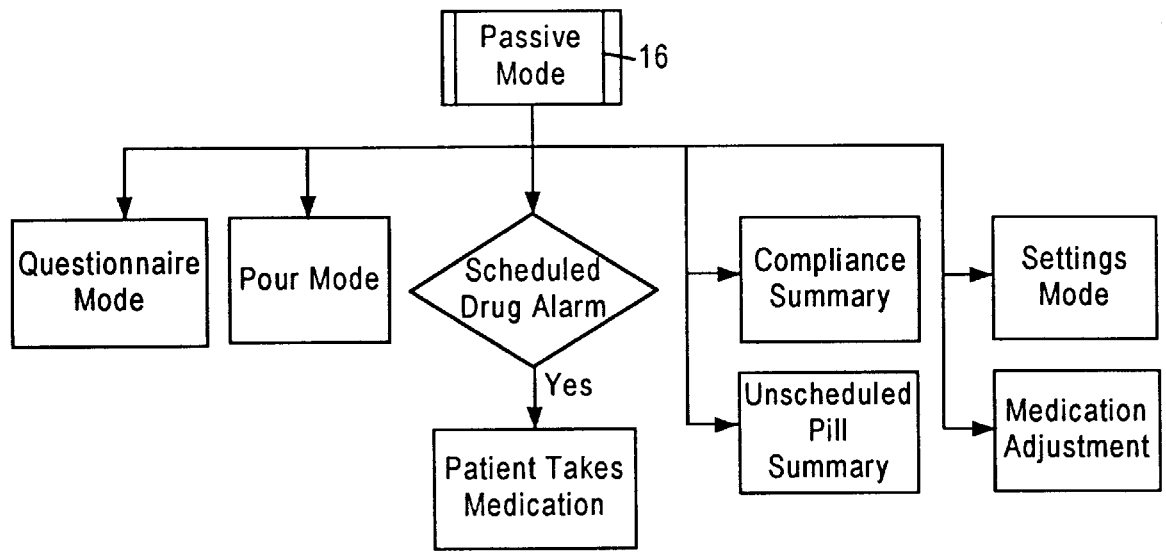
FIG. 4 illustrates a flow chart of the general operation of the medical monitoring device, operating system and method of the present invention.
Figure 5:
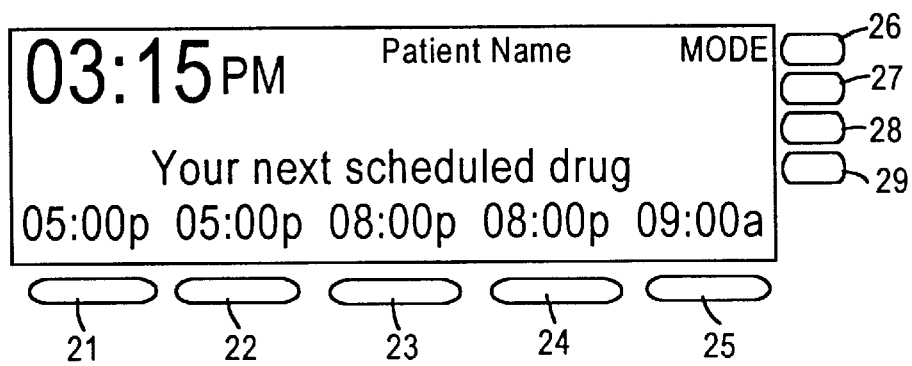
FIG. 5 illustrates the liquid crystal display, dedicated keys and soft function keys in the passive mode of the medical monitoring device, operating system and method of the present invention.

Referring to FIGS. 4 and 5, once programmed, the device remains in a passive mode 61 from which one of a plurality of events can occur. In the passive mode 61, the device displays the current time of day, the patient's name and the patient's upcoming medication schedule. In an alternative embodiment, the device may also display the date. The display of the patient's drug schedule comprises a display, located directly above each dedicated key, of the next prescribed time that the patient should take the medication contained in the medication compartment associated with that key. For example, as illustrated in FIG. 5, the time of day is 3:15 pm, and the patients drug schedule entails taking the medication contained in compartments 21 and 22 at 5:00 pm, compartments 23 and 24 at 8:00 pm and compartment 25 at 9:00 am the following morning.

Figure 6A:
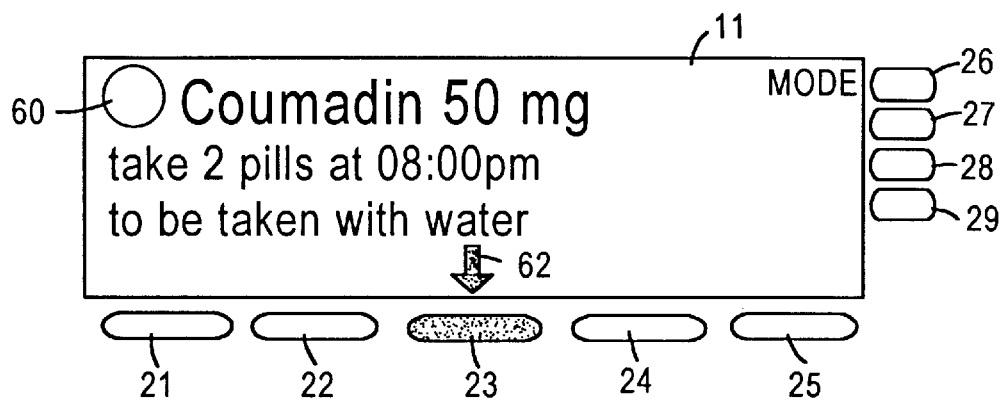
FIGS. 6(a)–(c) illustrate the liquid crystal display, dedicated keys and soft function keys during a dedicated key operating sequence of the medical monitoring device, operating system and method of the present invention.

From the passive mode 61, the patient can readily obtain information concerning any of the medications contained in the medication compartments by actuating or pressing the dedicated key associated with the medication regarding which the information is sought. When the patient actuates or presses a dedicated key one time, the device displays a prescription label message concerning the medication contained in the medication compartment associated with the actuated key. For example, as illustrated in FIG. 6(a), if the patient actuates dedicated key 23, the device displays the name of the medication contained in the associated medication compartment 33 ("Coumadin 50 mg"), the prescribed schedule for that particular medication ("take 2 pills at 08:00 pm"), a graphic representation and indication of the color of the medication 60, information concerning the optimum conditions for taking the medication ("to be taken with water"), and an arrow 62 pointing to the dedicated key actuated and associated medication compartment. If the patient does not actuate any other keys for a predetermined wait period (preferably approximately from 5–30 seconds), then the device returns to passive mode 61.

Figure 6B:
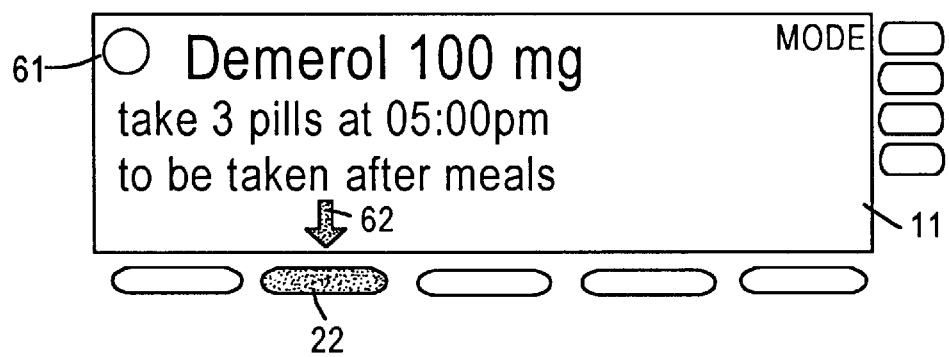

If the patient then actuates a different dedicated key, either within the predetermined wait period or after that period of time, the device displays the label message concerning the medication contained in the medication compartment associated with that key. For example, as illustrated in FIG. 6(b), if the patient actuates dedicated key 22, the device displays the name of the medication contained in the associated medication compartment 32 ("Demerol 100 mg"), the prescribed schedule for that particular medication ("take 3 pills at 05:00 pm"), a graphic representation and indication of the color of the medication 61, information concerning the optimum conditions for taking the medication ("to be taken after meals"), and an arrow 62 pointing to the actuated dedicated key and associated medication compartment. Then, as specified above, if the patient does not actuate any other keys for a predetermined wait period, the device returns to passive mode.

Figure 6C:
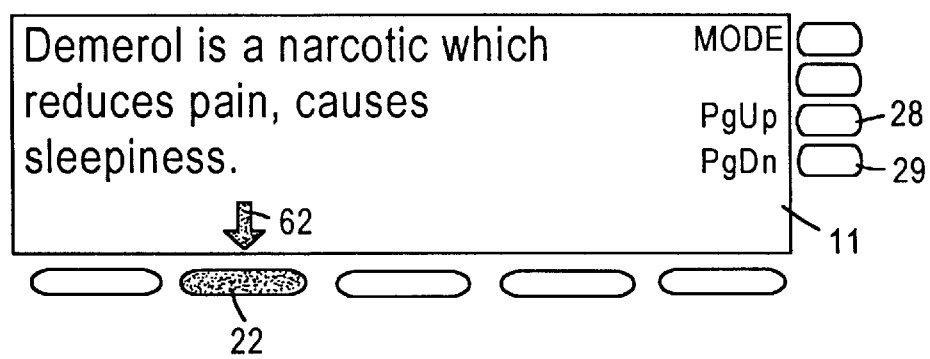

If the patient actuates the same dedicated key 22, within the predetermined wait period relative to the first actuation, then the device displays additional information concerning the medication contained in the associated medication compartment. For example, as illustrated in FIG. 6(c), if the patient actuates dedicated key 22 within the predetermined wait period relative to the first actuation, the device displays descriptive information concerning the medication contained in the associated medication compartment (Demerol). Also, the controller assigns page up and page down functions to the soft function keys 28 and 29, respectively. Actuation of the page up and page down soft function keys 28 and 29 causes the microcontroller 10 to scroll through screen displays containing additional information concerning the associated medication. Then, as specified above, if the patient does not actuate any other keys for the predetermined wait period, the device returns to passive mode.

Further successive actuations of a same dedicated key will access additional information concerning the medication contained in the medication compartment associated with the actuated key. The additional information may include information about the particular medical condition that the medication treats (i.e. general information about the medical condition, information about how the medication impacts the condition, and information about the patient's prognosis based on adherence to the prescribed medication schedule). Further information may concern potential side effects and adverse reactions associated with the particular medication, the process of diagnosing or treating the medical condition, harmful or adverse interaction with other medications, and laboratory procedures or other diagnostic tests involved in diagnosing and treating the medical condition.

Also from the passive mode 61, an alarm may activate signaling the patient through visual and/or audible alert signals. The alarm may either be a scheduled medication alarm, or a general alarm. The scheduled medication alarm alerts the patient and indicates that certain scheduled medication doses are due to be taken. The general alarm alerts the patient and indicates that some other action is required. The other action may be one of several possibilities, including response to certain patient queries, performance of a particular test, placing the device within the cradle for communication with a remote device, phoning or making an appointment with the health care provider, giving an injection, inhaling an aerosolized medication, etc.

Figure 7A:
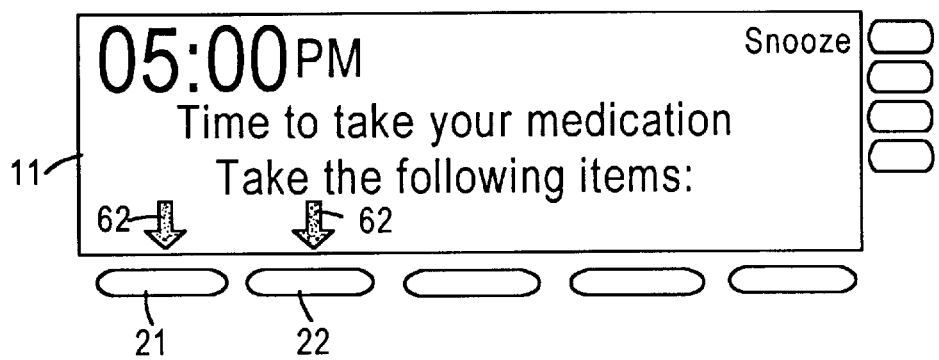
FIGS. 7(a)–(e) illustrate the liquid crystal display, dedicated keys and soft function keys during an operating sequence of a scheduled medication alarm operating sequence of the medical monitoring device, operating system and method of the present invention.
Figure 7B:
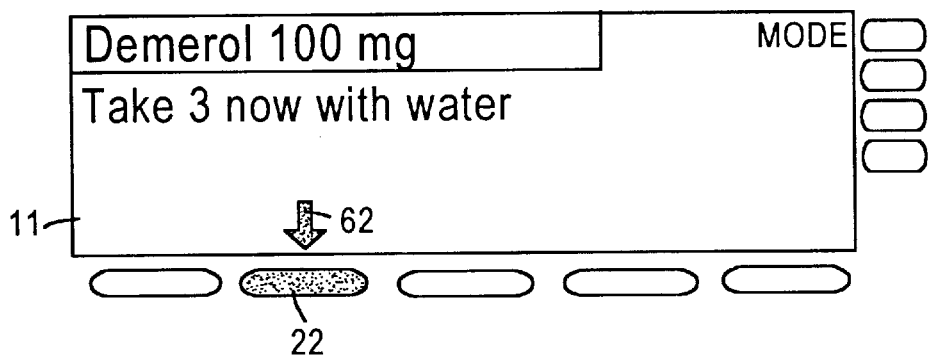
Figure 7C:
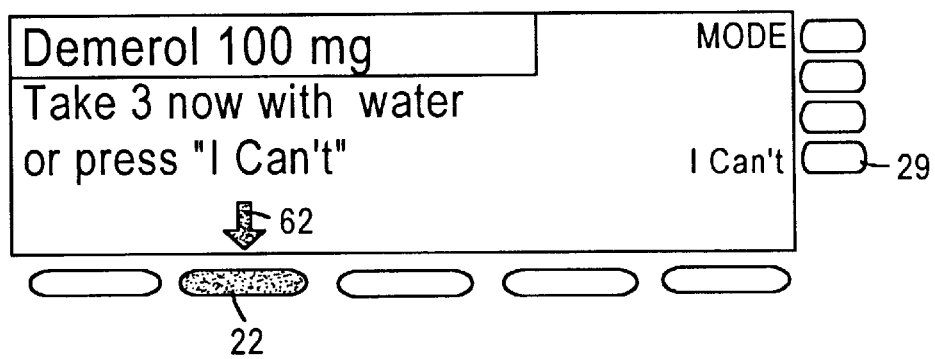
Figure 7D:
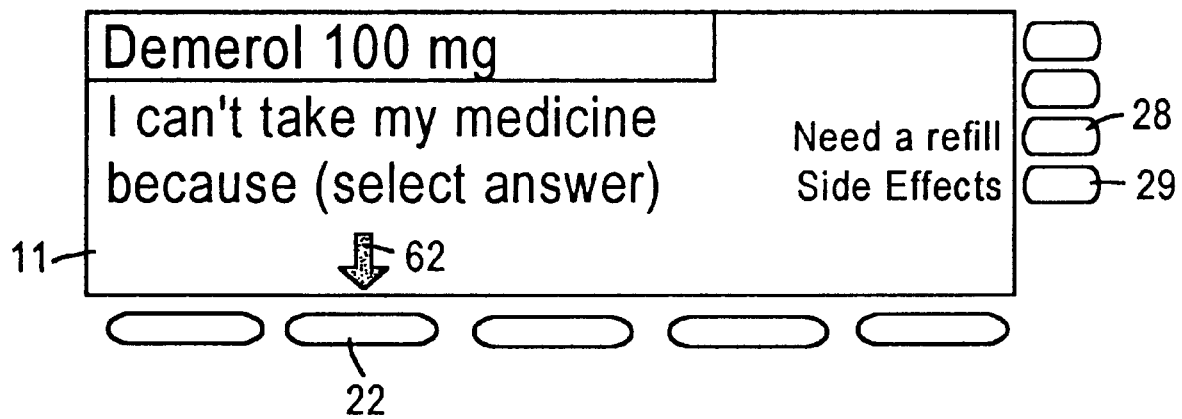
Figure 7E:
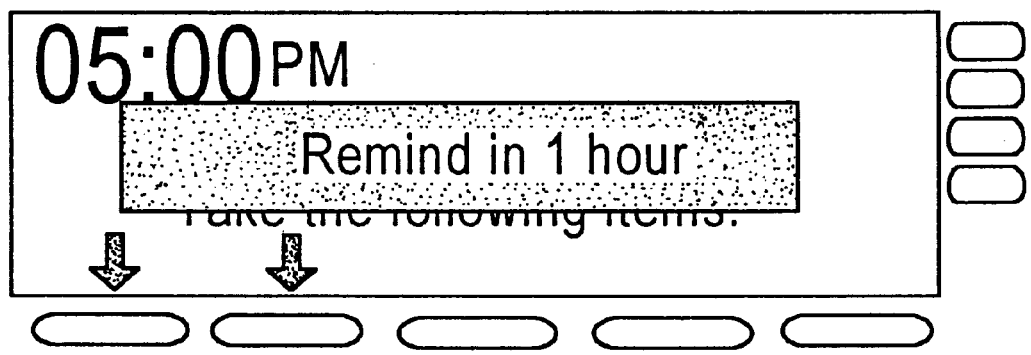

Referring to FIG. 7(a), when a scheduled medication alarm occurs, the device continues to display the current time, and displays a message indicating that scheduled medication(s) are due to be taken. The device designates the particular scheduled medications with arrows 62 pointing to the appropriate medication compartments. The patient can access specific information concerning the medications that are the subject of a scheduled medication alarm by actuating the dedicated key associated with one of those medications. Further, during a scheduled medication alarm, the microcontroller 10 assigns a snooze function to the soft function key 26, and actuation of the snooze key suspends the alarm for a predetermined period of time, previously programmed into the device (i.e. 1 hour), as illustrated in FIG. 7(e). The snooze function defaults to 15 minutes if not overridden during device programming. As illustrated in FIG. 7(b), upon actuating dedicated key 22, the device displays the name and strength of the medication in he upper left corner of the LCD 11 in reverse video, the prescription requirements for the associated medication, a request that the patient take the prescribed quantity at that time and any special instructions ("Take 3 now with water").

When the patient opens the appropriate medication compartments during a scheduled medication alarm, the compartment switch associated with each compartment signals the microcontroller 10. The microcontroller 10 then displays a message on the LCD 11, designating the prescribed quantity for the medication in the opened compartment and the conditions for taking the medication, as illustrated in FIG. 7(c). The message requests that the patient either take the designated quantity prescribed for the medication or alternatively actuate the soft function key 29 to indicate that the medication cannot be taken, as illustrated in FIG. 7(c).

Then, actuating the "I Can't" soft function key 29, signals the microcontroller 10, which displays an appropriate message. For example, as illustrated in FIG. 7(d), the message queries the patient as to why the scheduled medication cannot be taken, with the potential responses of "Need a refill" and "Side Effects" assigned to soft function keys 28 and 29, respectively. Actuating the soft function key assigned to a particular response signals the microcontroller 10 and indicates the patient's response, and the microcontroller 10 records the response along with other associated information (i.e. the particular medication to which the response relates and the time of day when the response was given). Actuating the soft function key 29 indicating that the patient is experiencing adverse reactions or side effects may then prompt the microcontroller 10 to query the patient as to the particular reactions or effects experienced, as illustrated in FIG. 8(c). The microcontroller 10 will again record the patient's response along with other associated data.

Opening and closing a designated compartment, during a scheduled medication alarm, signals the microcontroller 10, indicating that the patient adhered to the prescribed schedule for the medication contained in the compartment. The microcontroller 10 then records the patient's adherence accordingly. If the patient fails to obey a scheduled medication alarm and does not open and close each of the designated medication compartments, within a predetermined period of time or until the next scheduled medication alarm, then the alarm will continue at periodic intervals (i.e. 15 minutes). The alarm will also provide a visual signal (i.e. "MISSED MEDICATION"), informing the patient that a scheduled medication was not taken, and designating the appropriate compartment and necessary quantity. The device may display other messages on the LCD 11, warning the patient of the adverse consequences associated with the failure to adhere to the particular medication schedule. The scheduled medication alarm will deactivate once the patient accesses all of the designated medication compartments associated with the particular alarm.

In another embodiment of the present invention, the audible scheduled medication alarm signal includes the use of a transducer or voice generation chip and speaker that emits speech for giving audible instructions concerning the prescribed medications. In this embodiment, a number of common messages and/or words generally associated with prescription instructions are stored in the SRAM 13 or EPROM 12 (i.e. "Take," "Pill," "A," "Pills," "Water," "Juice," "Times," "One," "Two," "Day," etc.). The messages and/or words are stored in a table look-up format, and the device plays audible messages by sequencing through specific combinations (i.e. "Take Two Pills With Milk Two Times A Day"). Also, additional messages specific to particular medications could be programmed into the SRAM 13 or EPROM 12 for alerting the patient under certain predefined circumstances.

Figure 8A:
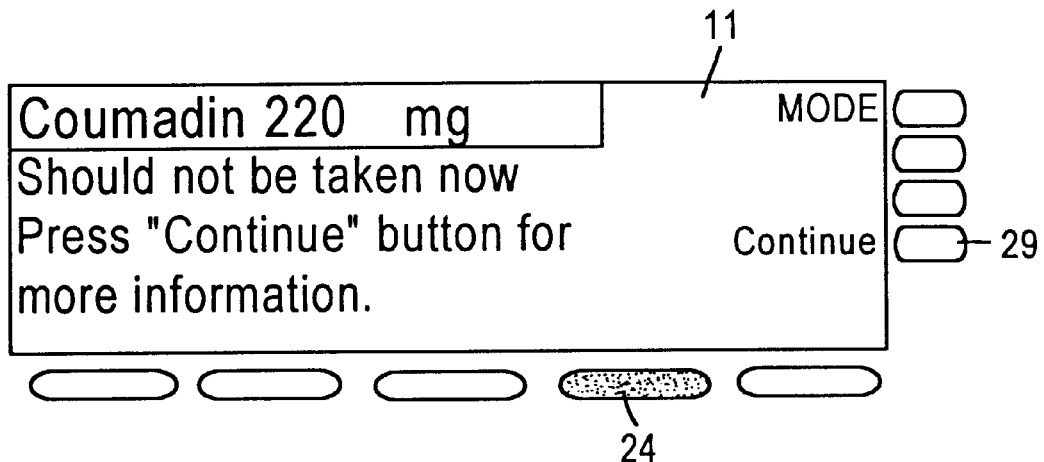
FIGS. 8(a)–(b) illustrate the liquid crystal display, dedicated keys and soft function keys during an unscheduled medication alarm operating sequence of the medical monitoring device, operating system and method of the present invention.
Figure 8B:
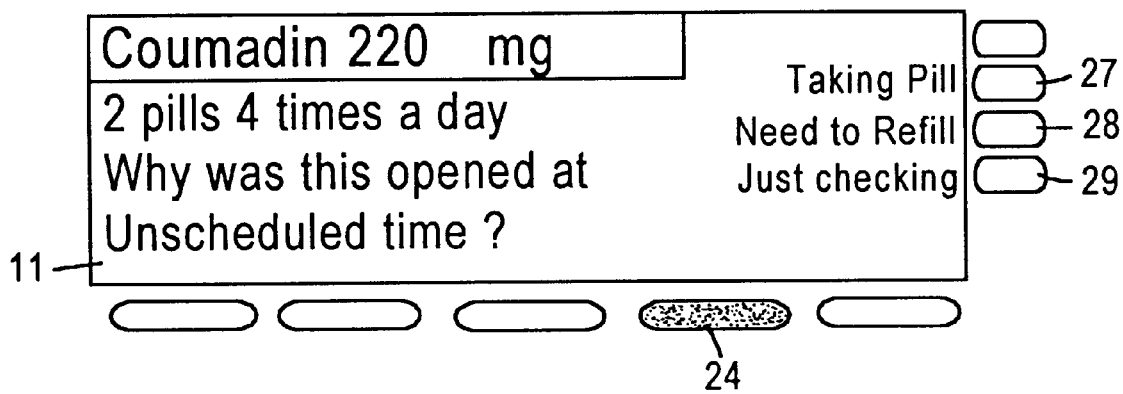

When the patient opens a medication compartment while the device is in the passive mode and no scheduled medication alarm is occurring, an unscheduled pill alarm occurs. During an unscheduled pill alarm, the device provides audible and visual signals. Referring to FIG. 8(a), the visual signals comprise a displayed message, with the medication label and strength in reverse video at the upper left corner of the LCD 11, along with a message that the medication should not be taken at that time. The device also displays a message indicating that the patient should actuate the "Continue" soft function key 29 for more information. Actuating the "Continue" soft function key initiates the display of the medication label and strength in reverse video at the upper left corner of the LCD 11, along with the prescribed medication schedule for the medication contained in the opened compartment. The device also displays a query as to why the compartment was opened, with potential responses assigned to particular soft function keys.

Figure 9A:
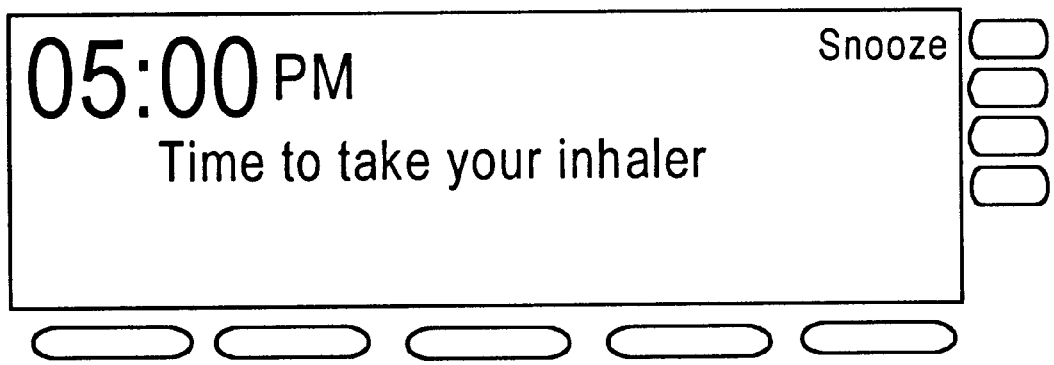
FIGS. 9(a)–(b) illustrate the liquid crystal display, dedicated keys and soft function keys during different general signals of the medical monitoring device, operating system and method of the present invention.
Figure 9B:
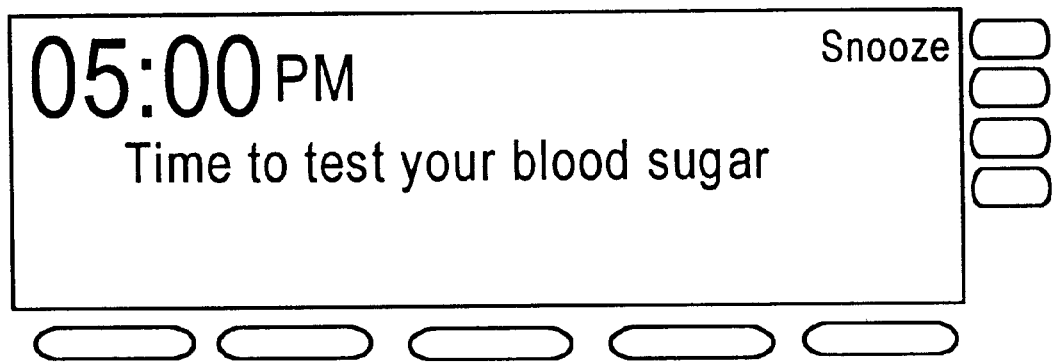

Other alarms occurring from the passive mode alert the patient concerning other medical related activities. For example, as illustrated in FIG. 9(a), an alarm can alert the patient that a dose of an inhaler is due to be taken. As illustrated in FIG. 9(b), additional alarms can remind the patient to perform certain tests, such as a blood sugar test.

Figure 10A:
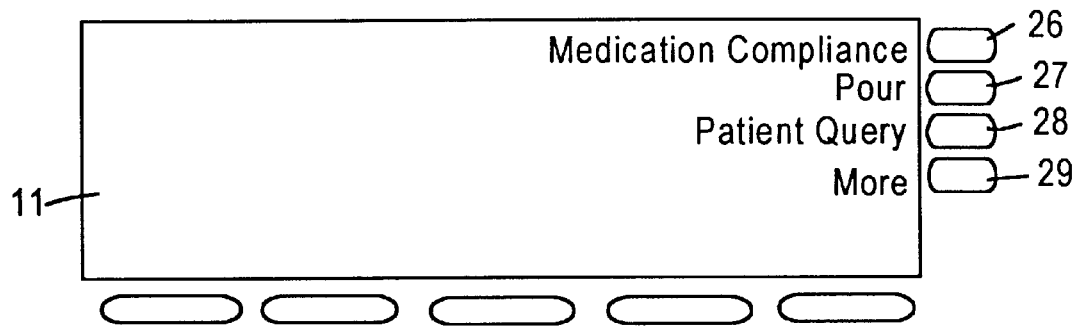
FIGS. 10(a)–(b) illustrate the liquid crystal display, dedicated keys and soft function keys during a mode-select function of the medical monitoring device, operating system and method of the present invention.
Figure 10B:
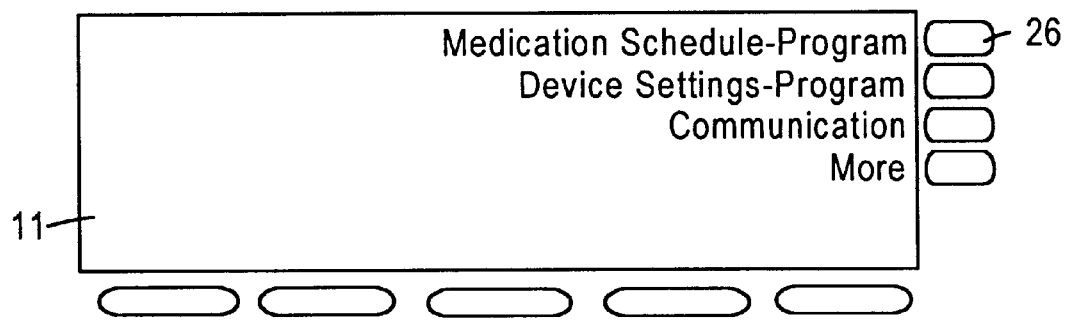

Further, while in the passive mode 61, soft function key 26 controls a mode-select function that initiates an active mode of operation whereby the patient initiates different operating modes of the device. Referring to FIG. 10(a), actuating the mode-select soft function key 26 from the passive mode displays a mode-select screen, wherein each soft function key is assigned a different mode-select function. Soft function key 26 initiates a "Medication Compliance" mode, soft function key 27 initiates a "Pour" mode (for refilling medication compartments), soft function key 28 initiates a "Patient Query" mode, and soft function key 29 is assigned a "More" function. Actuation of the "More" soft function key 29 scrolls the display for accessing additional modes of operation, as illustrated in FIG. 10(b). The additional modes of FIG. 10(b) are a "Medication Schedule—Program" mode, a "Device Settings—Program" mode, and a "Communication" mode.

Figure 11A:
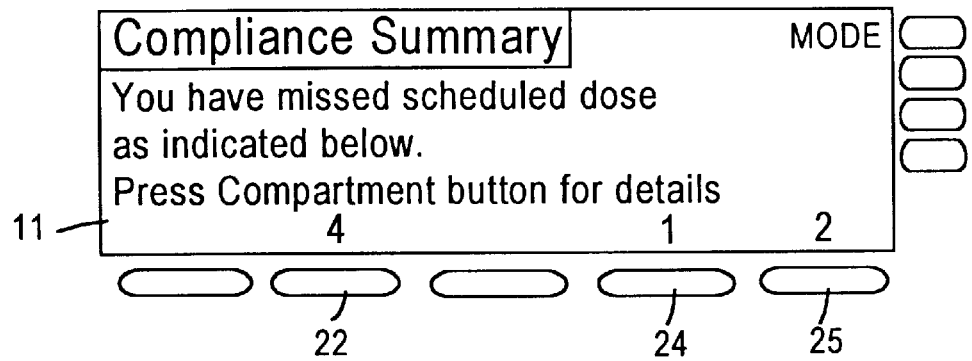
FIGS. 11(a)–(c) illustrate the liquid crystal display, dedicated keys and soft function keys during a "Medication Compliance" mode operating sequence of the medical monitoring device, operating system and method of the present invention.

Referring to FIG. 11(a), in the "Medication Compliance" mode, the device displays a summary screen with the title "Compliance Summary" displayed in reverse video in the upper left corner, and a synopsis of the patient's medication schedule adherence. Specifically, above each medication compartment containing a medication for which the patient missed scheduled doses, the device displays the number of missed doses for the medication contained in the associated compartment. For example, as illustrated in FIG. 11(a), the patient missed 4 doses of the medication in compartment 32 (the compartment associated with dedicated key 22), 1 dose of the medication in compartment 34 (the compartment associated with dedicated key 24) and 2 doses of the medication in compartment 35 (the compartment associated with dedicated key 25).

Figure 11B:
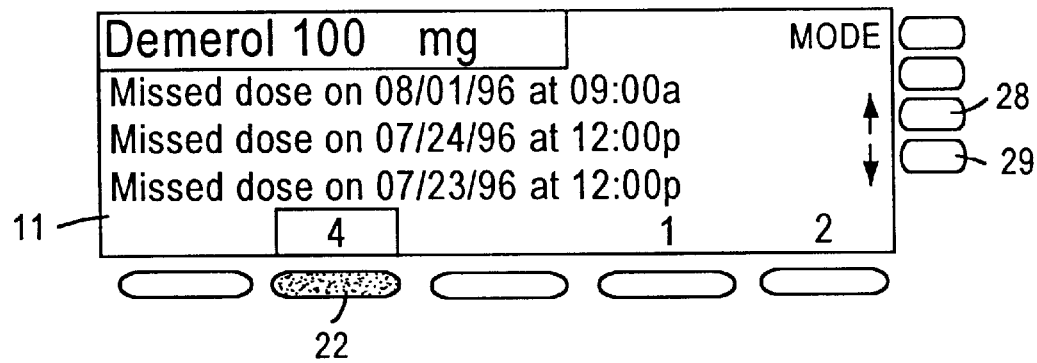
Figure 11C:
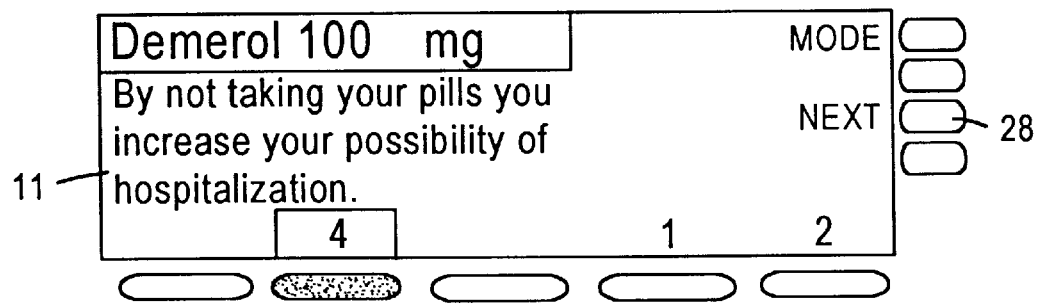
Figure 13A:
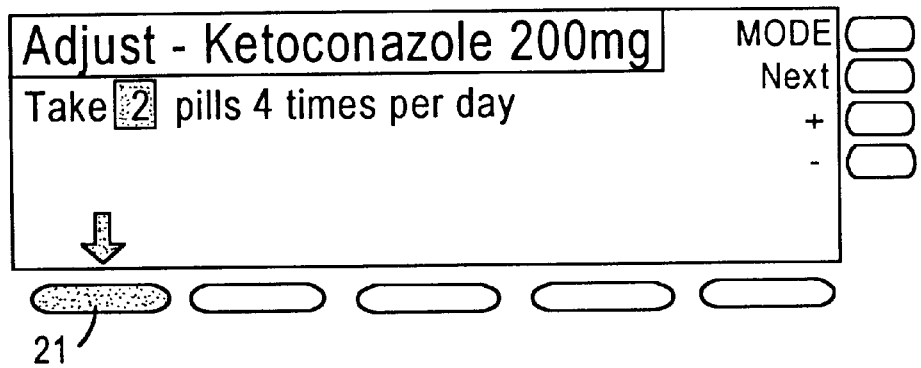
FIGS. 13(a)–(h) illustrate the liquid crystal display, dedicated keys and soft function keys during a "Medication Schedule—Program" mode operating sequence of the medical monitoring device, operating system and method of the present invention.
Figure 13B:
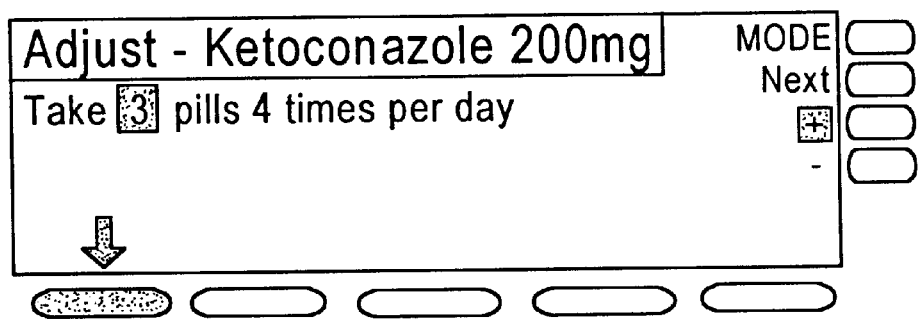
Figure 13C:
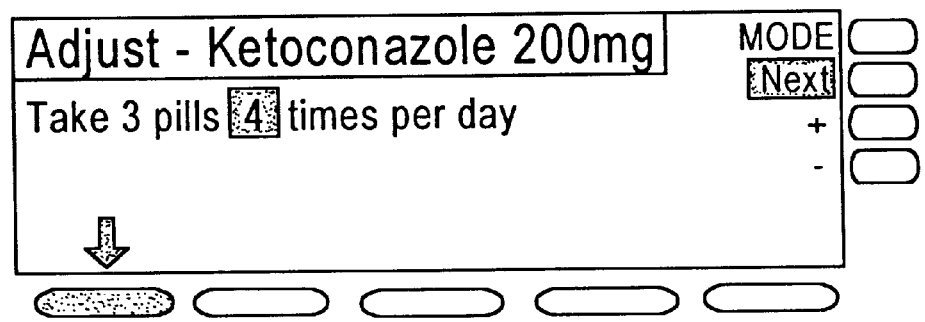
Figure 13D:
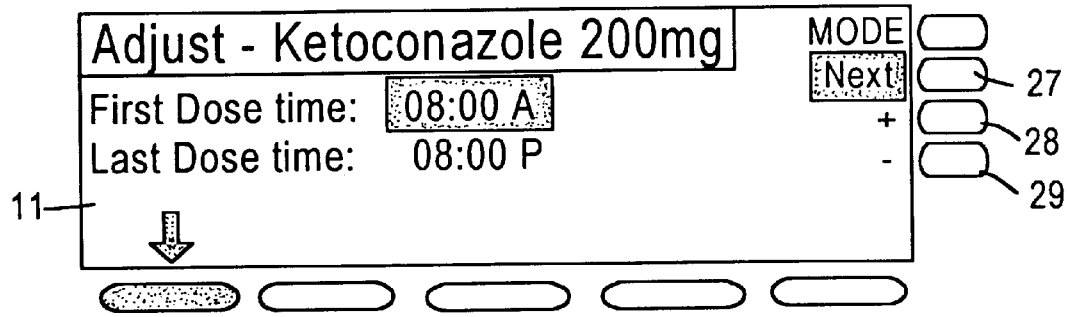
Figure 13E:
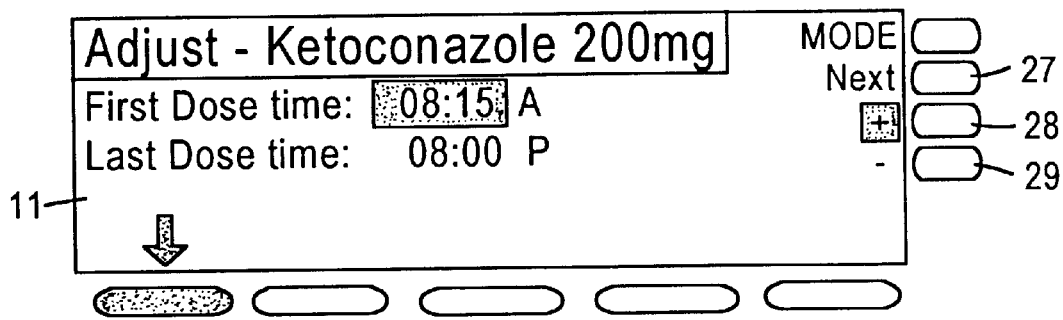
Figure 13F:
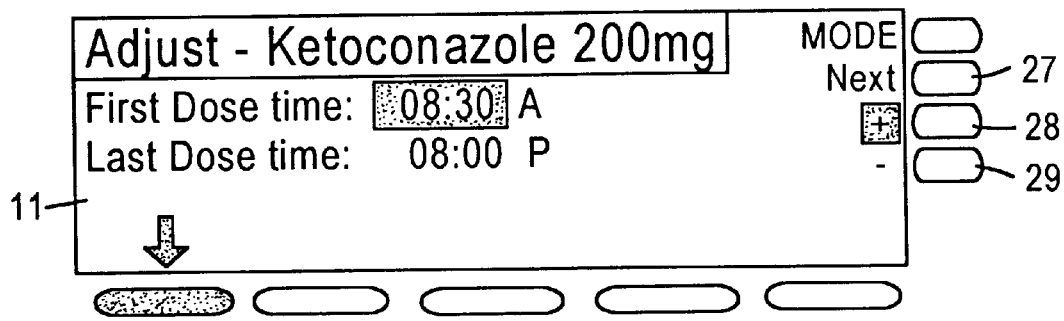
Figure 13G:
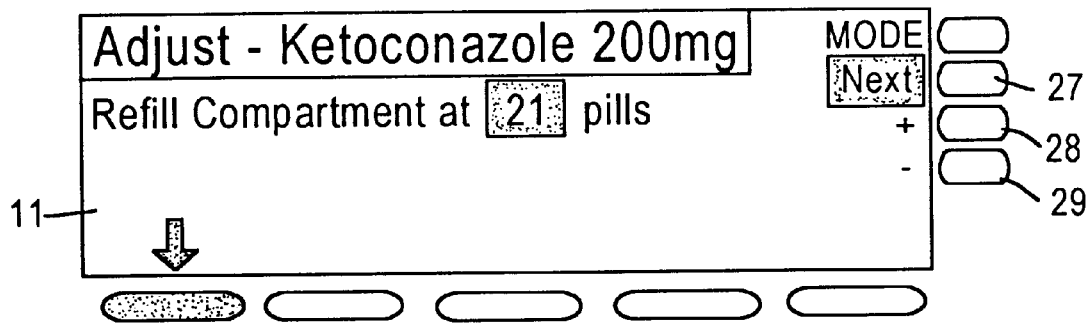
Figure 13H:
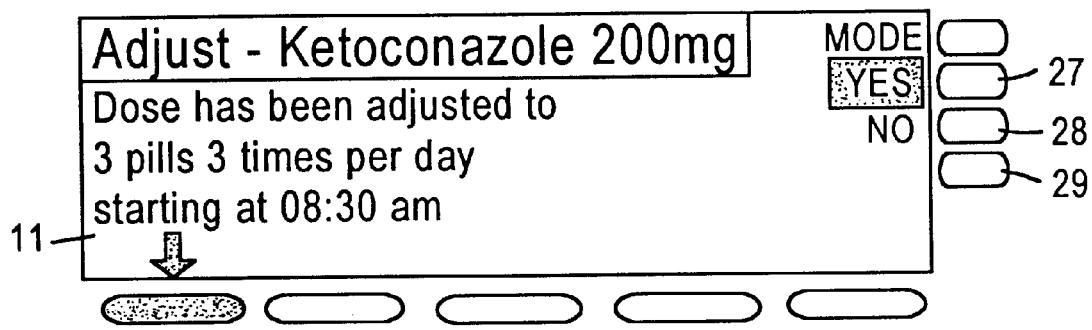

The patient then actuates a particular dedicated key to obtain the details concerning the missed schedules for the medication contained in the associated compartment. For example, as illustrated in FIG. 11(b), when dedicated key 22 is actuated, the device displays the name and strength of the associated medication in reverse video in the upper left corner of LCD 11, and displays messages indicating that the patient missed certain doses at specified dates and times. In this instance, since only three missed doses fit on the LCD screen, soft function keys 28 and 29 serve as scroll keys for scrolling up and down to review additional entries of missed medication doses. Further actuation of the dedicated key provides the patient information concerning the potential or likely consequences of missing the medication dose, as illustrated in FIG. 11(c). Additionally, soft function key 28 serves a "NEXT" function for accessing additional information concerning the missed doses of the particular medication. The device thereby provides educational information for motivating the patient to comply with the medication schedules.

Referring to FIGS. 12(a)–12(d), in the "Patient Query" mode, the device displays a series of questions concerning health status assessment, adverse effects or side effects experienced by the patient, treatment progress and the patient's general quality of life. Other questions that require responses from the health care provider may be posed. The questions are framed in either true/false (yes/no) format, scaling format or multiple choice format, and the soft function keys 26–29 are assigned particular responses according to the question format. Actuating a soft function key signals the microcontroller 10 and indicates the particular response chosen, and the microcontroller 10 records the patient's or health care provider's responses along with associated data (i.e. date and time of questioning). Questions may also be framed in decision tree format depending on the extent and complexity of the details necessary for the most efficient administration of medication, or administration of other components of the medical treatment plan, for treating a particular medical condition.

The "Communication" mode facilitates the transfer of data between the medical monitoring device and a remote device. During the communication mode the health care provider can download specific programming data associated with a particular patient's prescribed medication schedule and medical treatment regimens, and upload patient response data or other information, through the communications port 17.

Further, referring to FIGS. 13(*a*)–13(*f*), in the "Medication Schedule—Program" mode, the device allows the patient of health care provider to modify prescribed medication schedules for a particular medication. Actuating the dedicated key 21, while in the "Medication Schedule—Program" mode, facilitates the modification of the prescribed schedule for the medication contained in the associated medication compartment. The device displays an adjust message, with the name and strength of the medication being adjusted, in reverse video in the upper left corner of the LCD 11, and displays the current prescribed frequency ("Take 2 pills 4 times per day"), as illustrated in FIG. 13(*a*). The number of pills per dose "2" is highlighted, and actuating the "+" soft function key 28 or the "−" soft function key 29 raises or lowers the highlighted number by one for each actuation, accordingly. FIG. 13(*b*) illustrates the display after actuating the "+" soft function key 28 one time; the number of pills per dose is now "3" instead of "2" ("Take 3 pills 4 times per day"). Actuating the "Next" soft function key highlights the next setting (the frequency of doses per day) for modification, as illustrated in FIG. 13(*c*), and that setting is modified in the same manner.

The user can then set the dose times, by actuating the "Next" soft function key 27, as illustrated in FIGS. 13(*d*)–13(*f*). Referring to FIG. 13(*d*), the first dose time and last dose time are displayed on the LCD 11, with the first dose time highlighted. The fist dose time is changed in 15 minute increments by actuating the "+" and "−" soft function keys 28 and 29. The device automatically calculates the last dose time by adding 12 hours to the first dose time, and sets the intermediate dose times by dividing the 12 hour period by the scheduled number of doses per day. As illustrated in FIG. 13(*e*), actuating the "+" soft function key 28 one time increases the first dose time 15 minutes to "08:15 A", and, as illustrated in FIG. 13(*f*), actuating the "+" soft function key 28 another time increases the first dose time another 15 minutes to "08:30 A".

After setting the dose times, actuating the "Next" soft function key 27 allows for the modification of the refill amount, as illustrated in FIG. 13(*g*). The refill amount is highlighted on the LCD 11, and the "+" and "−" soft function keys 28 and 29 increase and decrease the refill amount, accordingly.

Referring to FIG. 13(*h*), after completion of the "Medication Schedule—Program" mode, the device displays the new settings, and requests that the user verify them by actuating the "Yes" soft function key 27. If the settings are incorrect, the user actuates the "No" soft function key 28, and the device returns to the beginning of the "Medication Schedule—Program" mode.

Further, the mode soft function key 26 enables the user to modify certain device settings or program information (i.e. date and time of day settings, alarm volume, snooze interval, etc.).

Figure 14A:
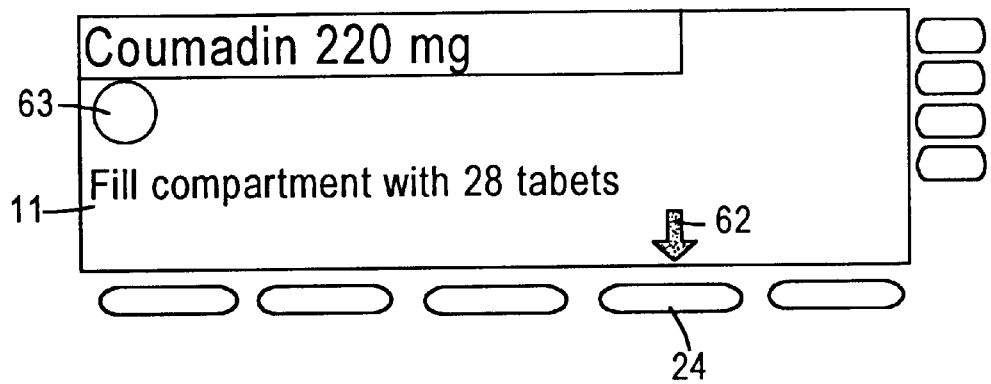
FIGS. 14(a)–(c) illustrate the liquid crystal display, dedicated keys and soft function keys during a "Pouring" alarm operating sequence of the medical monitoring device, operating system and method of the present invention.
Figure 14B:
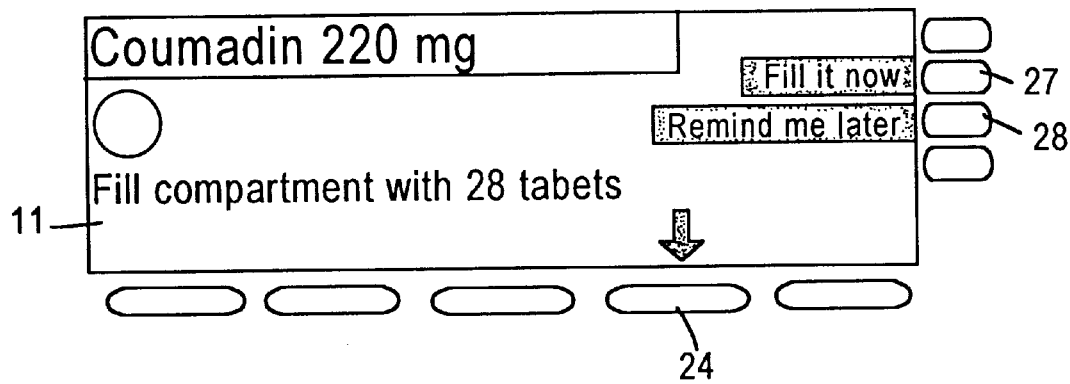
Figure 14C:
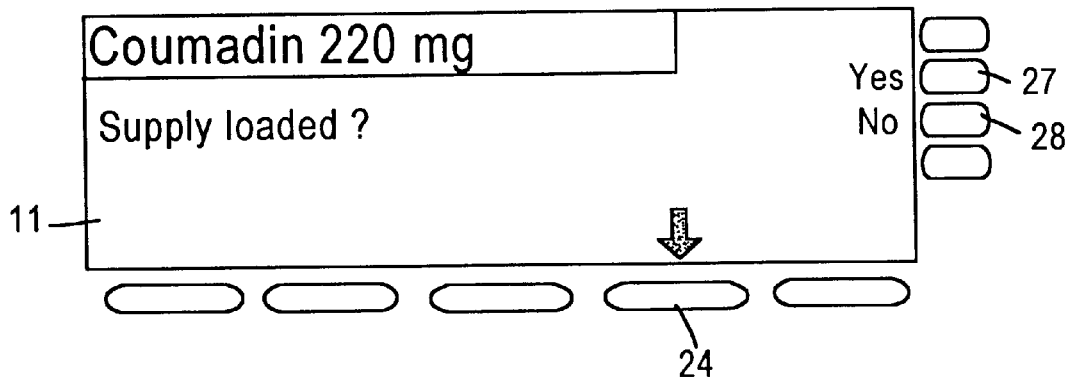

The device tracks the number of pills in each compartment as the patient complies with scheduled medication alarms. From the passive mode, when the device figures that a medication compartment is empty, the device provides a "pouring" alarm to alert the patient that it is time to refill a medication compartment, as illustrated in FIGS. 14(*a*)–14(*c*). Referring to FIG. 16(*a*), upon the occurrence of a "Pouring" alarm, the device displays the name and strength of the medication to be refilled in reverse video in the upper left corner of the LCD 11, along with a graphic representation of the medication 63. The device also indicates the number of pills to be refilled and displays an arrow pointing to the appropriate medication compartment (the medication compartment 34 associated with dedicated key 24).

The alarm continues until the user actuates the associated dedicated key 24. The device then allows the user to actuate the "Fill it now" soft function key 27, or the "Remind me later" soft function key 28, as illustrated in FIG. 14(*b*). If the user actuates the "Remind me later" soft function key 28, then the "Pouring" alarm will occur at a pre-programmed future amount of time (the default is 2 hours). The "Pouring" alarm will continue periodically until the user actuates the "Fill it now" soft function key 27, or unless the associated medication compartment is programmed to be empty. Actuating the "Fill it now" soft function key 27 redisplays the previous screen, and the associated medication compartment must be opened and closed to deactivate the "Pouring" alarm. Once the associated medication compartment is opened and closed, the device prompts the user to verify the supply load, as illustrated in FIG. 14(*c*). If the user verifies the supply load by indicating "Yes", then the device will continue tracking the inventory of the associated medication compartment. Otherwise, if the user verifies the supply load by indicating "No", then the device disables the inventory tracking function for the associated medication compartment.

Figure 15A:
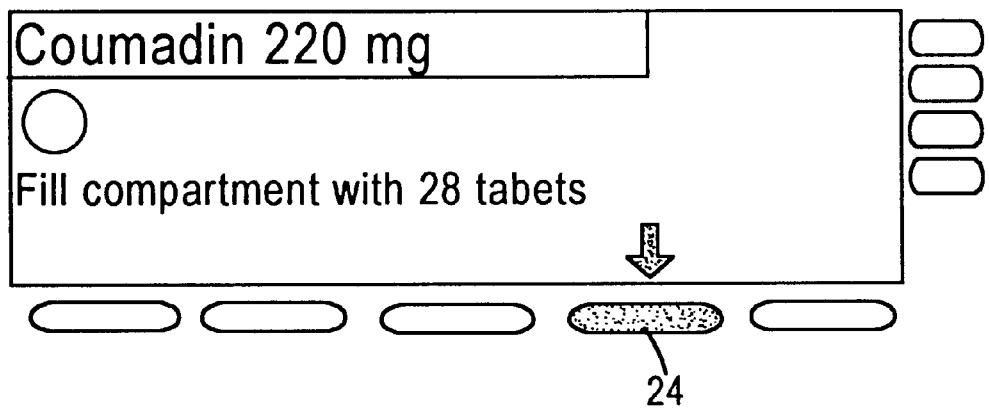
FIGS. 15(a)–(b) illustrate the liquid crystal display, dedicated keys and soft function keys during a "Pouring" mode operating sequence of the medical monitoring device, operating system and method of the present invention.
Figure 15B:
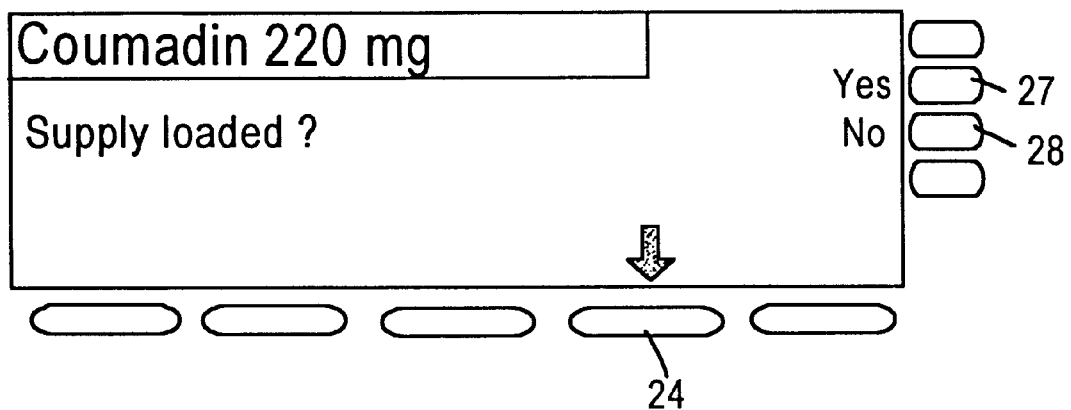

Referring to FIG. 10(*a*), the "Pouring" mode can be selected by actuating the "Pouring" mode soft function key 27, when the device is in the active mode (after actuation of the mode-select soft function key 26, from the passive mode). After user initiation of the "Pouring" mode, the user must actuate the dedicated key associated with the medication compartment to be refilled. As illustrated in FIG. 15(*a*), the device then displays the name and strength of the medication to be refilled in reverse video in the upper left corner of the LCD 11, along with a graphic representation of the medication 63. The device also indicates the number of pills to be refilled and displays an arrow pointing to the appropriate medication compartment (the medication compartment 34 associated with dedicated key 24). Once the associated medication compartment is opened and closed, the device prompts the user to verify the supply load, as illustrated in FIG. 15(*b*). If the user verifies the supply load by indicating "Yes", then the device will continue tracking the inventory of the associated medication compartment. Otherwise, if the user verifies the supply load by indicating "No", then the device disables the inventory tracking function for the associated medication compartment.

Figure 3:
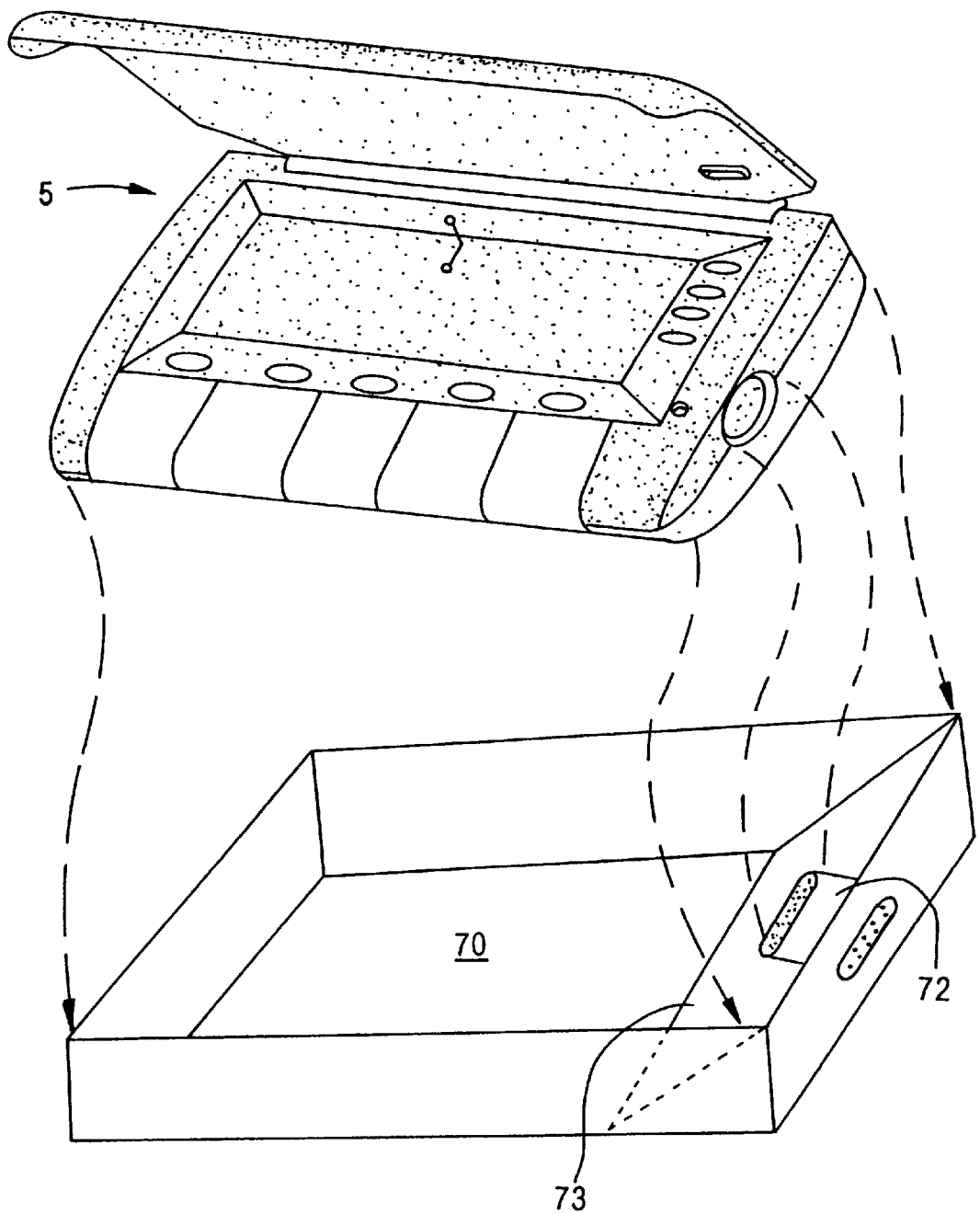
FIG. 3 illustrates the cradle of the present invention, and the interface between the cradle and medical monitoring device.

In a further embodiment of the present invention, as illustrated in FIG. 3, an electronic cradle 70 is provided for mounting the device 5 to facilitate automatic communications, programming and uploading. The cradle includes an interface 72 capable of transmitting data to, and receiving data from, the communications port 17. The cradle further includes a modem device 73. The cradle's modem device 73 can be programmed to automatically dial certain numbers at certain times and connect to remote devices, or be instructed to do so by the medical monitoring device. Once connected to a remote device, the cradle then provides patient identification information to the remote device, and either downloads programming data from the remote device, or uploads user response data to the remote device, or performs both downloading and uploading, automatically. The present invention thereby provides health care providers with the ability to automatically download a program to the patient's device, and upload information concerning the patient's treatment progress, from a remote location.

Of course, it should be understood that a wide range of modifications can be made to the exemplary embodiments described above. For example, a multitude of different menu, information and patient query schemes could be designed for the dedicated keys 21–25 and soft function keys 26–29. It is therefore intended that the foregoing detailed description be regarded as illustrative rather than limiting and that it be understood that it is the following claims, including all equivalents, which are intended to define the scope of this invention.

What is claimed is:

1. An operating system residing in a storage device, the operating system comprising instructions that initiate a controller of a medical monitoring device to display treatment messages on a display when one of a plurality of dedicated keys is actuated, the operating system associating each of the dedicated keys with a medical treatment regimen, and wherein a single actuation of one of the dedicated keys signals the operating system to initiate the display of a one of the treatment messages relating to the medical treatment regimen associated with the actuated dedicated key, said medical monitoring device for managing administration of the medical treatment regimens for treating a patient's medical conditions.

2. The operating system of claim 1, wherein a number of successive actuations of the one dedicated key signals the operating system to initiate the display of a different one of the treatment messages relating to the associated medical treatment regimen for each successive actuation.

3. An operating system for a medical monitoring device for managing administration of medication and medical treatment regimens to treat a patient's medical conditions, said operating system residing in a storage medium and comprising instructions that initiate a controller of the medical monitoring device to:

display treatment data on a display when one of a plurality of dedicated keys is actuated, the operating system associating each of the dedicated keys with one of the medical treatment regimens, and the treatment data being related to the medical treatment regimen associated with the actuated dedicated key; and control modes of operation of the medical monitoring device, the modes of operation being initiated and executed in accordance with actuation of soft function keys.

4. The operating system of claim 3, wherein a number of successive actuations of the one dedicated key signals the operating system to initiate the display of different treatment data relating to the associated medical treatment regimen for each successive actuation.

5. The operating system of claim 3, wherein the instructions further initiate the controller to assign one of the modes of operation to each soft function key, and display an indication of the mode of operation assigned to each softfunction key, and, when one of the soft function keys is actuated, the instructions signal the controller to initiate and execute the mode of operation assigned to the actuated soft function key.

6. The operating system of claim 5, wherein the instructions further initiate the controller to assign a "More" function to one of the soft function keys, and, when the "More" soft function key is actuated, the instructions initiate the controller to assign a different one of the modes of operation to each soft function key except for the "More" soft function key.

7. The operating system of claim 3, wherein, when a soft function key assigned to a medication schedule adherence mode is actuated, the instructions initiate the controller to display information concerning the patient's adherence to the medical treatment regimens.

8. The operating system of claim 7, wherein, when one of the dedicated keys is subsequently actuated within a predetermined time period after actuation of the soft function key assigned to the medication schedule adherence mode, the instructions initiate the controller to display information concerning adherence to the medical treatment regimen associated with the actuated dedicated key.

9. The operating system of claim 8, wherein, when the one dedicated key is actuated a number of successive times within the predetermined period, the instructions initiate the controller to display further information concerning adherence to the medical treatment regimen associated with the actuated dedicated key for each successive actuation.

10. The operating system of claim 3, wherein, when a soft function key assigned to a query mode of operation is actuated, the instructions initiate the controller to display patient query data, assign potential patient responses to the soft function keys, and receive and process patient response data according to an at least one soft function key actuated in response to the displayed patient query data.

11. The operating system of claim 3, wherein, when a soft function key assigned to a communication mode of operation is actuated, the instructions initiate the controller to execute a communication mode of operation, wherein the controller controls the transmission and receipt of data through a communication port.

12. The operating system of claim 3, wherein, when a soft function assigned to a programming mode of operation is actuated, the instructions initiate the controller to execute a programming mode for changing device settings.

13. The operating system of claim 3, wherein each associated treatment regimen comprises a prescribed medication.

14. The operating system of claim 13, wherein the instructions further initiate the controller to provide scheduled medication signals according to a prescribed medication schedule stored in the device for each prescribed medication, each scheduled medication signal including the display of treatment messages indicating prescribed medications due to be taken.

15. The operating system of claim 14, wherein, during a scheduled medication signal, when one of the dedicated keys associated with one of the prescribed medications due to be taken is actuated, the instructions initiate the controller to display treatment data relating to the associated prescribed medication.

16. The operating system of claim 15, wherein, during a scheduled medication signal, when the one dedicated key is actuated a number of successive times within a predetermined time period, the instructions cause the controller to display further treatment data relating to the associated prescribed medication for each successive actuation.

17. The operating system of claim 14, wherein, during a scheduled medication signal, the instructions initiate the controller to assign an "I Can't" function to one of the soft function keys, wherein, actuation of the "I Can't" soft function key signals the instructions to initiate the controller to display patient query data, assign potential patient responses to the soft function keys, and receive and process patient response data according to an at least one soft function key actuated in response to the displayed patient query data.

18. The operating system of claim 17, wherein the instructions further initiate the controller to display further patient query data, the content of which depending upon the processing of the patient response data, assign further potential patient responses to the soft function keys, and receive and process further patient response data according to an at least one soft function key actuated in response to the displayed further patient query data.

* * * * *